United States Patent
Mayer et al.

(10) Patent No.: US 6,648,925 B1
(45) Date of Patent: Nov. 18, 2003

(54) COLORING AGENT COMPRISING TRANSITION METALS

(75) Inventors: Bernd Mayer, Duesseldorf (DE); Peter Kuhm, Hilden (DE); Horst Hoeffkes, Duesseldorf (DE); Gertrud Ewald, Solingen (DE); Hans-Oscar Stephan, Duisburg (DE); Melita Heller, Duesseldorf (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 0 days.

(21) Appl. No.: 09/869,132

(22) PCT Filed: Dec. 14, 1999

(86) PCT No.: PCT/EP99/09903
§ 371 (c)(1),
(2), (4) Date: Sep. 26, 2001

(87) PCT Pub. No.: WO00/38630
PCT Pub. Date: Jul. 6, 2000

(30) Foreign Application Priority Data

Dec. 23, 1998 (DE) .......................................... 198 59 681

(51) Int. Cl.$^7$ ................................................. A61K 7/13
(52) U.S. Cl. ....................... 8/405; 8/406; 8/408; 8/621; 8/623; 8/624; 8/627; 8/628; 8/631
(58) Field of Search ........................... 8/405, 406, 408, 8/621, 623, 627, 628, 631, 624

(56) References Cited

U.S. PATENT DOCUMENTS

| | | | |
|---|---|---|---|
| 3,429,646 A | 2/1969 | Steed | 8/10 |
| 4,865,774 A | 9/1989 | Fabry et al. | 252/554 |
| 4,931,218 A | 6/1990 | Schenker et al. | 252/551 |
| 5,294,726 A | 3/1994 | Behler et al. | 554/98 |
| 5,534,267 A | 7/1996 | Neunhoeffer et al. | 424/701 |
| 5,676,706 A | * 10/1997 | Akram et al. | 8/416 |
| 5,715,845 A | 2/1998 | Samain | 132/204 |
| 6,099,592 A | 8/2000 | Vidal et al. | 8/409 |

FOREIGN PATENT DOCUMENTS

| | | |
|---|---|---|
| DE | 36 42 097 | 6/1988 |
| DE | 37 23 354 | 1/1989 |
| DE | 37 25 030 | 2/1989 |
| DE | 39 26 344 | 2/1991 |
| DE | 195 34 214 | 10/1996 |
| DE | 197 56 455 | 3/1999 |
| DE | 197 57 510 | 6/1999 |
| EP | 0 507 448 | 10/1992 |
| EP | 0 621 029 | 10/1994 |
| EP | 0 548 620 | 4/1995 |
| EP | 0 740 931 | 11/1996 |
| FR | 1439307 | 8/1966 |
| JP | 61-69718 | 10/1986 |
| JP | 1-317443 | 12/1989 |
| JP | 3-246217 | 1/1991 |
| WO | WO 94/08970 | 4/1994 |

OTHER PUBLICATIONS

Derwent WPI database, Accession No. 1990–040675 [06], abstract of JP 01 317443 (1990).
Patent Abstracts of Japan, of JP 01 317443, (Dec. 22, 1990).
Derwent WPI database, Accession No. 1991–365788 [50], abstract of JP 03 246217 (1991).
Patent Abstracts of Japan, of JP 03 246217, (Nov. 1, 1991).
Patent Abstracts of Japan, vol. 010, No. 235, of JP 61 069718, (Apr. 10, 1986).
Derwent WPI database, Accession No. 1986–133805 [21], abstract of JP 61 069718 (1986).
The Science of Hair Care, Chapter 7, pp. 235–261, published as vol. 7 of Dermatology, Marcel Dekker Inc., NY/Basel (1986).
The Science of Hair Care, Chapter 8, pp. 263–286 published as vol. 7 of Dermatology, Marcel Dekker, Inc. NY/Basel (1986).
EU Inventory of Cosmetic Ingredients, Colipa, Mar. (1996) on diskette.
K. Schrader, Grundlagen un Rezepturen der Kosmetika (Bases and Formulations in Cosmetics), $2^{nd}$ Edition, pp. 782–799, Huethig Buch Berlag, Heidelberg, Germany (1989).

* cited by examiner

*Primary Examiner*—Yogendra N. Gupta
*Assistant Examiner*—Eisa Elhilo
(74) *Attorney, Agent, or Firm*—Stephen D. Harper

(57) ABSTRACT

The present invention relates to a composition for coloring keratin fibers and a method of using the same. The composition of the present invention contains at least one dye precursor, and one or more clathrate compounds that contain transition metal complexes.

19 Claims, No Drawings

COLORING AGENT COMPRISING TRANSITION METALS

CROSS REFERENCE TO RELATED APPLICATIONS

This application is a national stage application under 35 U.S.C. §371 of international application PCT/EP99/09903 filed on Dec. 14, 1999, the international application not being published in English. This application also claims priority under 35 U.S.C. §119 to DE 198 59 681.2, filed on Dec. 23, 1998.

FIELD OF THE INVENTION

This invention relates to colorants containing transition metal complexes included in clathrate compounds as oxidation catalysts and to the use of these compositions for coloring keratin-containing fibers.

BACKGROUND OF THE INVENTION

In general, keratin-containing fibers, for example wool, pelts and in particular human hair, are colored either with substantive dyes or with oxidation dyes which are formed by oxidative coupling of one or more primary intermediates with one another or with one or more secondary intermediates.

Substantive dyes are applied under moderate conditions. Unfortunately, their disadvantage is that the colors obtained often have inadequate fastness properties. Although intensive colors with good fastness properties can be obtained with oxidation dyes, the color is generally developed under the effect of $H_2O_2$ or $H_2O_2$ adducts, which can result in damage to the fibers.

Oxidation colorants using atmospheric oxygen as a very mild oxidizing agent have also been proposed. However, oxidation with atmospheric oxygen is generally incomplete. In oxidation hair colorants in particular, which are generally applied in a cream-like cosmetic carrier, the atmospheric oxygen comes up against considerable diffusion barriers. In addition, it has been proposed, for example in EP-B1 0 548 620, to limit the hydrogen peroxide content of the oxidation colorants to 1% by weight or less, but at the same time to add special enzymes, peroxidases, to the colorant for activation. Unfortunately, none of these proposals has yet produced a significant breakthrough in terms of a competitive market product.

Accordingly, there is still a need for oxidation colorants which, by virtue of their relatively low content of oxidizing agents or by oxidation with atmospheric oxygen, enable coloring to be carried out under more moderate conditions without adversely affecting the final coloring result. In addition, it is highly desirable to reduce the pH of the colorants to a value around the neutral point in order to prevent possible damage to the fibers through the normally strong alkalinity of the colorants.

The use of transition metal complexes in connection with the oxidative coloring of hair is known in principle. For example, it was proposed in European patent application EP-A2-507 448 to treat the hair before the actual coloring process with a transition metal complex containing the ligands 2,2'-dipyridyl or o-phenanthroline in order to stabilize the hair against oxidative degradation of the cysteine. In addition, it was proposed in German patent DE-C1-195 34 214 to use transition metal complexes as oxidation catalysts in hair colorants containing derivatives of 4-(2,5-diaminophenoxymethyl)-1,3-dioxolane as primary intermediates. Finally, it was proposed in German patent application 197 57 510.2 to use transition metal complexes with ligands of the salen type as oxidation catalysts. In all these coloring preparations, the transition metal cations are present in free form and, potentially, may accumulate on or in the hair. However, this may be regarded as in no way optimal in terms of minimizing the damage potential of the colorants. Accordingly, there was a need to develop oxidation catalysts for hair colorants which would only lead to a very low concentration of free transition metal cations in the preparation to be applied.

SUMMARY OF THE INVENTION

It has now been found that, by using transition metal complexes included in cavities of clathrate compounds in oxidation colorants, the quantity of oxidizing agent can be greatly reduced and/or coloring can be carried out with atmospheric oxygen as sole oxidizing agent or coloring can be carried out in the neutral pH range.

The compositions according to the invention are further distinguished by the low concentration of free transition metal cations in the preparation to be applied.

In a first embodiment, therefore, the present invention relates to compositions for coloring keratin fibers, more particularly human hair, which contain at least one dye precursor and 0.0001 to 1.0% by weight of a transition metal cation with at least two stable oxidation stages included in cavities of clathrate compounds which is complexed with at least one multidentate ligand.

DETAILED DESCRIPTION OF THE INVENTION

According to the invention, multidentate ligands are molecules which have two or more electron donor centers.

Preferred transition metals are iron, cobalt, copper, manganese, molybdenum, ruthenium and/or vanadium; complexes with iron and, more particularly, with copper or ruthenium as transition metal have proved to be particularly suitable for the purposes of the invention.

Preferred clathrate compounds in which the transition metal complexes are included are inter alia zeolites of type A, K, L, P-L, O, T, X, Y and Ω and mixtures thereof, the choice of the suitable clathrate compound being determined by the size of the transition metal complex to be included. It is crucial that, in the production of the included complexes, both the transition metal ion and the ligands necessary for complexing are able to enter the cavity of the clathrate compound whereas the complex in the process of formation may no longer pass through the opening of the cavity in order to guarantee stable inclusion of the complex. The sizes of the cavities of the various zeolites are known in principle to the expert. For example, the zeolite Y preferred for the purposes of the invention has cavities with diameters of ca. 1.3 nm of which the openings have a diameter of 0.74 nm. By "stable inclusion" is meant that no quantities of free complex influencing the oxidation catalysis can be detected under in-use conditions, i.e. in the hair treatment preparation. The transition metal complexes being formed in, and then included in, the cavities of the clathrate compounds are far more stable and hence effective over a longer period than the same transition metal complexes which have been applied to the surface of carrier materials even though these carrier materials are the same clathrate compounds.

Ligands which may be used in the transition metal complexes suitable for use in accordance with the invention are typical inorganic and organic substances. Besides carboxylates, organic ligands in such complexes include in particular compounds containing primary, secondary and/or tertiary amine and/or alcohol functions, such as pyridine, pyridazine, pyrimidine, pyrazine, imidazole, pyrazole, triazole, 2,2'-bispyridylamine, tris-(2-pyridylmethyl)amine, 1,4,7-triazacyclononane, 1,4,7-trimethyl-1,4,7-triazacyclononane, 1,5,9-trimethyl-1,5,9-triazacyclododecane, (bis-((1-methylimidazol-2-yl)-methyl))-(2-pyridylmethyl)-amine, N,N'-(bis-(1-methylimidazol-2-yl)-methyl)-ethylenediamine, N-bis-(2-benzimidazolyl-methyl)-aminoethanol, 2,6-bis-(bis-(2-benzimidazolylmethyl)aminomethyl)-4-methylphenol, N,N,N',N'-tetrakis-(2-benzimidazolylmethyl)-2-hydroxy-1,3-diaminopropane, 2,6-bis-(bis-(2-pyridylmethyl)-aminomethyl)-4-methyl-phenol, 1,3-bis-(bis-(2-benzimidazolylmethyl)aminomethyl)-benzene, sorbitol, mannitol, erythritol, adonitol, inositol, lactose and optionally substituted salens, porphines and porphyrines. Inorganic neutral ligands include, in particular, ammonia and water. The presence of at least one ammonia ligand is preferred, above all in the Co(III) complexes where the central atom is normally present with the coordination number 6. Unless all the coordination sites of the transition metal central atom are occupied by neutral ligands, a complex to be used in accordance with the invention contains other, preferably anionic ligands, more particularly mono- or bidentate ligands. These include, in particular, the halides, such as fluoride, chloride, bromide and iodide and the $(NO_2)^-$ group. In the context of the present invention, an $(NO_2)^-$ group may be both a nitro ligand which is attached to the transition metal through the nitrogen atom or a nitrito ligand which is attached to the transition metal through an oxygen atom. The $(NO_2)^-$ group may also be attached to a transition metal to form a chelate or may asymmetrically or $\mu^1$-O-bridge two transition metal atoms. Apart from the ligands mentioned, the transition metal complexes to be used in the activator system according to the invention may contain other ligands of generally more simple structure, more particularly monovalent or polyvalent anion ligands. Examples include nitrate, acetate, trifluoroacetate, formate, carbonate, citrate, perchlorate and complex anions, such as hexafluorophosphate. The anion ligands are necessary for the charge compensation between the transition metal central atom and the ligand system. The presence of oxo ligands, peroxo ligands and imino ligands is also possible. More particularly, such ligands can also have a bridging effect so that polynuclear complexes are formed. In the case of bridged binuclear complexes, the two metal atoms in the complex need not be the same. Binuclear complexes in which the two transition metal central atoms are the same or different and have different oxidation numbers may also be used.

In the absence of anion ligands or if the presence of anion ligands does not lead to complete charge compensation in the complex, anionic counterions which neutralize the cationic transition metal complex may be present in the transition metal complex compounds to be used in accordance with the invention. These anionic counterions include, in particular, nitrate, hydroxide, hexafluorophosphate, sulfate, chlorate, perchlorate, the halides, such as chloride, or the anions of carboxylic acids, such as formate, acetate, benzoate or citrate.

According to the invention, ligands containing at least one nitrogen atom as coordination site are preferred.

In one embodiment of the present invention, ligands containing at least one non-aromatic coordination site can be preferred. These ligands are better able to penetrate into the cavities of the clathrate compounds so that the formation of the catalysts according to the invention is promoted. In this embodiment, particularly preferred ligands are 1,4,8,11-tetraazacyclotetradecane 1,8-diazabicyclo[5.4.0]undec-7-ene (1,5-5)

ethylenediamine nitrilotriacetic acid tris(aminoethyl)amine tris(aminomethyl)methane 1,3,5-triaminocyclohexane and pyridine-2,6-dicarboxylic acid.

In a second preferred embodiment of the invention, ligands having at least one aromatic coordination site can be preferred. The transition metal complexes according to the invention with aromatic ligands are distinguished by increased stability and thus have a broader range of applications. Particularly preferred ligands with at least one aromatic coordination site are, for example, 2,2':6',2"-terpyridine 1,10-phenanthroline tris(2-pyridylmethyl)amine tris(2-pyridylethyl)amine and N-carboxymethyl-N-(2-pyridylmethyl)glycine.

In a first embodiment of the present invention, the dye precursor may be an oxidation dye precursor of the primary intermediate type. Several primary intermediates may also be used together in the compositions according to the invention.

Primary intermediates are normally aromatic or heterocyclic ring systems characterized by two reactive groups, generally hydroxy or amino groups, in the ortho or para position to one another. Examples of such compounds are primary aromatic amines with another free or substituted hydroxy or amino group in the para or ortho position, diaminopyridine derivatives, heterocyclic hydrazone derivatives or 4-aminopyrazolone derivatives.

According to the invention, preferred primary intermediates are p-phenylenediamine, p-toluylenediamine, p-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxymethylamino-4-aminophenol, 4,4'-diaminodiphenylamine, 4-amino-3-fluorophenol, 2-aminomethyl-4-aminophenol, 2-hydroxymethyl-4-aminophenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 4-amino-2-(2-hydroxyethoxy)-phenol and 4,5-diaminopyrazole derivatives according to EP 0 740 931 or WO 94/08970, for example 4,5-diamino-1-(2'-hydroxyethyl)-pyrazole.

Another preferred primary intermediate is 4-amino-2-((diethylamino)-methyl)-phenol.

Particularly preferred primary intermediates are p-phenylenediamine, p-toluylenediamine, p-aminophenol, 1-(2'-hydroxyethyl)-2,5-diaminobenzene, 4-amino-3-methylphenol, 2-aminomethyl-4-amino-phenol, 2,4,5,6-tetraaminopyrimidine, 2-hydroxy-4,5,6-triaminopyrimidine and 4-hydroxy-2,5,6-triaminopyrimidine.

The compositions according to the invention may additionally contain one or more secondary intermediates for shading the color tones obtained. Secondary intermediates are often aromatic or heterocyclic ring systems with two reactive groups in the meta position. The secondary intermediates generally used are m-phenylenediamine derivatives, naphthols, resorcinol and resorcinol derivatives, pyrazolones and m-aminophenol derivatives.

According to the invention, preferred secondary intermediates are 1-naphthol, pyrogallol, 1,5-, 2,7- and 1,7-dihydroxynaphthalene, o-aminophenol, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2-amino-3-hydroxypyridine, 2,6-dihydroxy-3,4-diaminopyridine, 3-amino-2-methylamino-6-methoxypyridine, 2,6-bis-(2-hydroxyethylamino)-toluene, 2,4-diaminophenoxyethanol, 1-methoxy-2-amino-4-(2-hydroxyethylamino)-benzene, 2-methyl-4-chloro-5-aminophenol, 6-methyl-1,2,3,4-tetrahydroquinoxaline, 3,4-methylenedioxyphenol, 3,4-methylenedioxyaniline, 2,6-dimethyl-3-aminophenol, 2-hydroxy-4-aminophenoxy ethanol, 2-methyl-5-(2-hydroxyethylamino)-phenol and 2,6-dihydroxy-3,4-dimethyl pyridine.

Particularly preferred secondary intermediates are 1-naphthol, 1,5-,2,7- and 1,7-dihydroxynaphthalene, 5-amino-2-methylphenol, resorcinol, 3-aminophenol, 4-chlororesorcinol, 2-chloro-6-methyl-3-aminophenol, 2-methyl resorcinol, 5-methyl resorcinol, 2,5-dimethyl resorcinol and 2,6-dihydroxy-3,4-diaminopyridine.

The primary and secondary intermediates are normally used in free form. However, compounds containing amino groups may preferably be used in salt form, more particularly in the form of the hydrochlorides and sulfates.

The hair colorants according to the invention contain both the primary intermediates and the secondary intermediates in a quantity of preferably 0.005 to 20% by weight and more preferably 0.1 to 5% by weight, based on the oxidation colorant as a whole. The primary intermediates and secondary intermediates are generally used in a substantially equimolar ratio to one another. Although it has proved to be of advantage to use the primary and secondary intermediates in an equimolar ratio, there is no disadvantage in using individual oxidation dye precursors in a certain excess so that primary intermediates and secondary intermediates may be present in the colorant in a molar ratio of preferably 1:0.5 to 1:2. The total quantity of oxidation dye precursors is generally at most 20% by weight, based on the colorant as a whole.

In a second preferred embodiment of the present invention, the dye precursor may be an indoline derivative corresponding to formula (Ia):

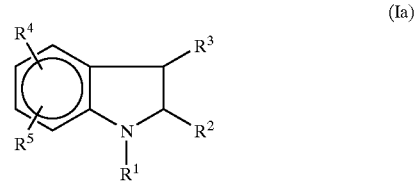

(Ia)

in which—independently of one another—$R^1$ is hydrogen, a $C_{1-4}$ alkyl group or a $C_{1-4}$ hydroxyalkyl group, $R^2$ is hydrogen or a —COOH group, the —COOH group optionally being present as a salt with a physiologically compatible cation, $R^3$ is hydrogen or a $C_{1-4}$ alkyl group, $R^4$ is hydrogen, a hydroxy group, an amino group, a $C_{1-4}$ alkoxy group or a group —OCO-$R^6$, where $R^6$ is a $C_{1-4}$ alkyl group, and $R^5$ is one of the groups mentioned for $R^4$, with the proviso that $R^4$ and $R^5$ are not both hydrogen, or a physiologically compatible salt of these compounds with an organic or inorganic acid.

In a third preferred embodiment of the present invention, the dye precursor may be an indole derivative corresponding to formula (Ib):

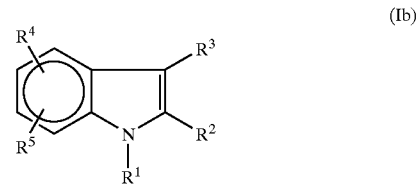

(Ib)

n which—independently of one another—$R^1$ is hydrogen, a $C_{1-4}$ alkyl group or a $C_{1-4}$ hydroxyalkyl group, $R^2$ is hydrogen or a —COOH group, the —COOH group optionally being present as a salt with a physiologically compatible cation, $R^3$ is hydrogen or a $C_{1-4}$ alkyl group, $R^4$ is hydrogen, a hydroxy group, an amino group, a $C_{1-4}$ alkoxy group or a group —OCO-$R^6$, where $R^6$ is a $C_{1-4}$ alkyl group, and $R^5$ is one of the groups mentioned for $R^4$, with the proviso that $R^4$ and $R^5$ are not both hydrogen, or a physiologically compatible salt of these compounds with an organic or inorganic acid.

Preferred compounds of formula (Ia) are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-aminoindoline. Particularly preferred compounds of formula (Ib) are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

5,6-Dihydroxyindole and 5,6-dihydroxyindoline are most particularly preferred.

In a first preferred variant of the embodiments described above, the compositions are formulated in such a way that they only contain indole and/or indoline derivatives of formulae (Ia) and (Ib) as oxidation dye precursors and are free from typical oxidation dye precursors of the primary intermediate/secondary intermediate type.

In a second preferred variant of the embodiments described above, the compositions according to the invention also contain typical oxidation dye precursors of the primary intermediate/secondary intermediate type in addition to the indole and/or indoline derivatives of formulae (Ia) and (Ib).

In a particularly preferred embodiment of the invention, the indole or indoline derivatives of formulae (Ia) and (Ib) may be used in combination with one or more secondary intermediates in hair colorants. Attention is specifically drawn by way of example at this juncture to the secondary intermediates mentioned above.

In another preferred embodiment of the invention, the indole and/or indole derivatives of formulae (Ia) and (Ib) may be used in combination with at least one amino acid or one oligopeptide in hair colorants. The amino acid is advantageously an α-amino acid; most particularly preferred α-amino acids are arginine, ornithine, lysine and histidine.

In another preferred embodiment, the hair colorants according to the invention may contain typical substantive dyes in addition to the dye precursors to further modify the shades. Substantive dyes are normally nitrophenylendiamines, nitroaminophenols, azo dyes, anthraquinones or indophenols. Preferred substantive dyes are the compounds known under the International names or trade names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene.

The colorants according to the invention of this embodiment contain the substantive dyes in a quantity of preferably 0.01 to 20% by weight, based on the colorant as a whole.

The compositions according to the invention may also contain naturally occurring dyes such as, for example, henna red, henna neutral, henna black, camomile blossom, sandalwood, black tea, black alder bark, sage, logwood, madder root, catechu, sedre and alkanet.

The dye precursors or the substantive dyes do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting compositions according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basel, 1986, and to the "Europäische Inventar der Kosmetik-Rohstoffe" published by the Europäische Gemeinschaft and available in disk form from the Bundesverband Deutscher Industrie- und Handelsunternehmen für Arzneimittel, Reformwaren und Körperpflegemittel d.V., Mannheim.

Particularly deep colors can be obtained if, besides the dyes and/or dye precursors, the colorants also contain a meadowfoam oil (INCI name: Meadowfoam Seed Oil).

To produce the colorants according to the invention, the dye precursors may be incorporated in an aqueous, alcoholic or aqueous/alcoholic carrier. For coloring hair, such carriers are, for example, creams, emulsions, gels or even surfactant-containing foaming solutions, for example shampoos, foam aerosols or other formulations suitable for application to the hair.

In the context of the invention, aqueous/alcoholic solutions are aqueous solutions containing 3 to 70% by weight of a $C_{1-4}$ alcohol, more particularly ethanol or isopropanol.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly preferred.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and generally ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—$(CH_2—CH_2O)_x$—$CH_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—$O(CH_2—CH_2O))_x$—$SO_3H$, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

In the context of the invention, zwitterionic surfactants are surface-active compounds which contain at least one quaternary ammonium group and at least one $—COO^{(-)}$ or $-SO_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one $—COOH$ or $—SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl amino-propionate, cocoacyl aminoethyl aminopropionate and $C_{12-18}$ acyl sarcosine.

Examples of the cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex® and the products marketed under the name of Dehyquart® are also readily biodegradable.

One example of a quaternary sugar derivative suitable for use as a cationic surfactant is the commercially available product Glucquat® 100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Depending on the nature of the colorant and the surfactant type, the surfactants are normally present in the colorants according to the invention in total quantities of 0.5 to 30% by weight, based on the colorant as a whole.

In a preferred embodiment, the hair treatment compositions according to the invention additionally contain a conditioning principle selected from the group consisting of cationic surfactants, cationic polymers, alkyl amidoamines, paraffin oils, vegetable oils and synthetic oils.

Cationic polymers can be preferred conditioning principles. They are generally polymers which contain a quaternary nitrogen atom, for example in the form of an ammonium group. Preferred cationic polymers are, for example, quaternized cellulose derivatives commercially available under the names of Celquat® and Polymer JR®. The compounds Celquat® H 100, Celquat® L 200 and Polymer JR® 400 are preferred quaternized cellulose derivatives.

polymeric dimethyl diallyl ammonium salts and copolymers thereof with esters and amides of acrylic acid and methacrylic acid. The products commercially obtainable as Merquat® 100 (poly(dimethyl diallyl ammonium chloride)) and Merquat® 550 (dimethyl diallyl ammonium chloride/acrylamide copolymer) are examples of such cationic polymers.

copolymers of vinyl pyrrolidone with quaternized derivatives of dialkylaminoacrylate and methacrylate such as, for example, vinyl pyrrolidone/ dimethylaminomethacrylate copolymers quaternized with diethyl sulfate. Such compounds are commercially obtainable under the names of Gafquat® 734 and Gafquat® 755.

vinyl pyrrolidone/methoimidazolinium chloride copolymers commercially obtainable under the name of Luviquat®.

quaternized polyvinyl alcohol and the polymers containing quaternary nitrogen atoms in the polymer main chain known by the names of polyquaternium 2, polyquaternium 17 polyquaternium 18 and polyquaternium 27.

Cationic polymers belonging to the first four of these groups are particularly preferred.

Other suitable conditioning principles are silicone oils, more particularly dialkyl and alkylaryl siloxanes such as, for example, dimethyl polysiloxane and methylphenyl polysiloxane and alkoxylated and quaternized analogs thereof. Examples of such silicone oils are the products marketed by Dow Corning under the names of DC 190, DC 200, DC 344, DC 345 and DC 1401 and the commercial products Q2-7224 (manufacturer: Dow Corning; a stabilized trimethyl silyl amodimethicone), Dow Corning® 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt: diquaternary polydimethyl siloxanes, quaternium-80).

Paraffin oils and vegetable oils, such as jojoba oil, sunflower oil, orange oil, almond oil, wheat germ oil and peach kernel oil, may also be used as conditioning agents.

Other suitable hair-conditioning compounds are phospholipids, for example soya lecithin, egg lecithin and kephalins.

Finally, the colorants according to the invention also contain a fatty compound.

Preferred fatty compounds are linear and branched, saturated and unsaturated fatty alcohols or natural fatty alcohol mixtures containing 8 to 22 carbon atoms in the alkyl chain such as, for example, decanol, octanol, octenol, dodecenol, decenol, octadienol, dodecadienol, decadienol, oleyl alcohol, erucyl alcohol, ricinolyl alcohol, stearyl alcohol, isostearyl alcohol, palmityl alcohol, lauryl alcohol, myristyl alcohol, arachidyl alcohol, caprylic alcohol, capric alcohol, linoleyl alcohol, linolenyl alcohol and behenyl alcohol, and the Guerbet alcohols and fatty alcohol cuts which are obtained by reduction of naturally occurring triglycerides, such as bovine tallow, palm oil, peanut oil, rapeseed oil, cottonseed oil, soybean oil, sunflower oil and linseed oil or fatty acid esters formed from esterification products thereof with corresponding alcohols and which therefore represent a mixture of different fatty alcohols. The fatty alcohols are normally used in quantities of 0.01 to 15% by weight, preferably in quantities of 0.1 to 10% by weight and more preferably in quantities of 0.3 to 6% by weight, based on the preparation as a whole.

Monoesters of fatty acids with alcohols containing 6 to 24 carbon atoms and triglycerides of natural origin may also be used as fatty compounds.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, zwitterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, symmetrical and non-symmetrical, linear and branched dialkyl ethers containing in all between 12 and 36 carbon atoms and more particularly 12 to 24 carbon atoms, for example di-n-octyl ether, di-n-decyl ether, di-n-nonyl ether, di-n-undecyl ether and di-n-dodecyl ether, n-hexyl-n-octyl ethers, n-octyl-n-decyl ether, n-decyl-n-undecyl ether, n-undecyl-n-dodecyl ether and n-hexyl-n-undecyl ether and also di-tert.butyl ether, diisopentyl ether, di-3-ethyldecyl ether, tert.butyl-n-octyl ether, isopentyl-n-octyl ether and 2-methylpentyl-n-octyl ether, antidandruff agents, such as piroctone olamine, zinc omadine and climbazole, animal and vegetable protein hydrolyzates, more especially elastin, collagen, keratin, milk protein, soya protein, almond protein and wheat protein hydrolyzates and fatty acid condensates and quaternized derivatives thereof, vitamins and vitamin precursors, such as panthenol, derivatives thereof and biotin, plant and honey extracts such as, in particular, extracts of oak bark, stinging nettle, hamamelis, hops, camomile, burdock root, horse willow, lime blossom, almond, aloe vera, coconut, mango, apricot, lemon, wheat, kiwi, melon, orange, grapefruit, sage, rosemary, birch, lady's-smock, creeping thyme, bloodwort, restharrow, meristem, ginseng and ginger root, other active principles, such as ceramides, allantoin, pyrrolidone carboxylic acids and bisabolol, UV filters, defoamers, such as silicones, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose, maleic acid and lactic acid, perfume oils, dimethyl isosorbide and cyclodextrins, solubilizers, such as ethanol, isopropanol, ethylene glycol, propylene glycol, glycerol and diethylene glycol, alkalizing agents such as, for example, ammonia, monoethanolamine, 2-amino-2-methylpropanol and 2-amino-2-methylpropane-1,3-diol, other substances for adjusting the pH value, cholesterol, swelling and penetration agents, such as glycerol, propylene glycol monoethyl ether, carbonates, hydrogen carbonates, guanidines, ureas and primary, secondary and tertiary phosphates, consistency factors, such as sugar esters, polyol esters or polyol alkyl ethers, structurants, such as-maleic acid, mono-, di- and oligosaccharides, fats and waxes, such as spermaceti, beeswax, montan wax and paraffins, fatty acid alkanolamides, opacifiers, such as latex, styrene/PVP and styrene/acrylamide copolymers, pearlizers, such as ethylene glycol monostearate and distearate and PEG-3-distearate, complexing agents, such as EDTA, NTA, β-alanine diacetic acid and phosphonic acids, reducing agents such as, for example, thioglycolic acid and derivatives thereof, thiolactic acid, cysteamine, thiomalic acid and α-mercaptoethanesulfonic acid, oxidizing agents, such as hydrogen peroxide, potassium bromate and sodium bromate, propellants, such as propane/butane mixtures, $N_2O$, dimethyl ether, $CO_2$, $N_2$ and air.

Information on other ingredients and quantity ranges for the individual ingredients can be found in the reference books known to the expert, for example K. Schrader, Grundlagen und Rezepturen der Kosmetika, 2nd Edition, Hüthig Buch Verlag, Heidelberg, 1989.

Basically, the color may be oxidatively developed with atmospheric oxygen. However, a chemical oxidizing agent is preferably used, particularly when human hair is to be not only colored, but also lightened. Particularly suitable oxidizing agents are hydrogen peroxide or addition products thereof with urea, melamine or sodium borate. Oxidation may also be carried out with enzymes. In this case, the enzymes may be used both to produce oxidizing per compounds and to enhance the effect of an oxidizing agent present in small quantities. One example of an enzymatic process is the procedure whereby the effect of small quantities (for example 1% and less, based on the composition as a whole) of hydrogen eroxide is enhanced by peroxidases.

According to the invention, the oxidation catalysts according to the invention may be made up both in a single preparation with the dye precursors and also separately.

In a preferred embodiment of the teaching according to the invention, the oxidation catalysts made up separately are dissolved in a suitable solvent, for example in water, ethanol or acetone and the resulting solution is stirred with the oxidizing agent preparation immediately before coloring of the hair. This preparation is then mixed with a preparation containing the dye precursors. The resulting ready-to-use hair coloring preparation should preferably have a pH in the range from 6 to 10, a pH of 6.5 to 8 being particularly preferred. The application temperatures may be in the range from 15 to 40° C. After a contact time of about 30 minutes, the hair colorant is removed by rinsing from the hair to be colored. There is no need for the hair to be washed with a shampoo where a carrier of high surfactant content, for example a coloring shampoo, has been used.

In the particular case of hair which is difficult to color, the preparation containing the oxidation dye precursors may be applied to the hair without preliminary mixing with the oxidation component. The oxidation component is applied after a contact time of 20 to 30 minutes, optionally after rinsing. After another contact time of 10 to 20 minutes, the hair is rinsed and, if desired, shampooed.

The present invention also relates to the use of the compositions described above for coloring keratin fibers.

By using the transition metal complexes in accordance with the invention, it is possible to obtain the coloring performance normally only obtained under alkaline conditions in the neutral pH range also or to achieve a more moderate coloring treatment by virtue of the fact that, in the alkaline range, the desired coloring performance is achieved with a far lower, i.e. up to 75% lower, concentration of oxidizing agent. For example, the concentration of hydrogen peroxide in a ready-to-use preparation can be reduced from about 3% by weight to about 1.0% by weight.

EXAMPLES

1. Production of the Catalysts 100 g of zeolite Y were stirred for 3 to 5 hours at room temperature with ca. 1,000 ml of a 1% by weight copper(II) chloride solution. The zeolite was then filtered off under suction and was washed with water until free from chloride (detection with $AgNO_3$ solution in nitric acid). In order to free the zeolite from externally adhering metal ions, the metal-doped zeolite was repeatedly washed with a 5% by weight sodium chloride solution. The re-exchange is terminated when no more metal can be detected in the filtrate. The zeolite was then rewashed until free from chloride, dried for 18 hours at 110° C. in a recirculating air drying cabinet and, finally, was calcined to constant weight at 250° C.

The copper content of the metal-doped zeolite was determined by X-ray fluorescence analysis. 1,8-Diazabicyclo [5.4.0]undec-7-ene (DBU for short) was then added to the metal-doped zeolite so that a molar ratio of Cu to DBU of 1:2.5 was obtained, followed by stirring for several hours at 80° C. in a water jet vacuum (80–100 mbar) in a rotary evaporator. The excess DBU was then washed out with water to the neutral point and the product was dried for 8 hours at 110° C. in a recirculating air drying cabinet.

The product had the following composition:

4.14% by weight carbon (C)

1.03% by weight nitrogen (N)

1.10% by weight copper (Cu)

This corresponds to a molar ratio of C to N to Cu of 19.9:4.3:1 and hence to a molar ratio of Cu to DBU of 1:2.

2. Production of the Coloring Cream

A coloring cream with the following composition was prepared (all quantities in g unless otherwise indicated):

Mixture A

| | |
|---|---|
| Hydrenol ® D[1] | 8.50 g |
| Lorol ® techn.[2] | 2.00 g |
| Eumulgin ® B2[3] | 0.75 g |
| Texapon ® NSO[4] | 20.00 g |
| Dehyton ® K[5] | 12.50 g |
| Water | 30.00 g |

[1]$C_{16–18}$ fatty alcohol (INCI name: Cetearyl Alcohol) (HENKEL)
[2]$C_{12–18}$ fatty alcohol (INCI name: Coconut Alcohol) (HENKEL)
[3]Cetylstearyl alcohol containing ca. 20 EO units (INCI name: Ceteareth-20) (HENKEL)
[4]Lauryl ether sulfate, sodium salt (ca. 27.5% active substance; INCI name: Sodium Laureth Sulfate) (HENKEL)
[5]N,N-dimethyl-N-($C_{8–18}$-cocoamidopropyl)-ammonium acetobetaine (ca. 30% active substance; INCI name: Aqua (Water), Cocamidopropyl Betaine) (HENKEL)

The substances Hydrenol D, Lorol and Eumulgin B2 were melted at 80° C., mixed with the water heated to 80° C. containing Texapon NSO and Dehyton T and emulsified with vigorous stirring. The emulsion was then cooled with gentle stirring.

Mixture B

| | |
|---|---|
| Sodium sulfite | 1.00 g |
| Ammonium sulfate | 1.00 g |
| 5-Amino-2-methyl phenol | 0.003 mole |
| 4-Amino-2-aminomethyl phenol hydrochloride | 0.003 mole |
| Ammonia (25% solution) | to pH |
| Water | 10.00 |

The dye precursors were dissolved in the water which had been heated to 50° C. and to which the sodium sulfite, ammonium sulfate and ammonia had been added.

The dye precursor solution (mixture B) was added to the emulsion (mixture A), the required pH was adjusted with an ammonia solution and the whole was made up to 100 parts by weight with water. Stirring was continued until the temperature reached room temperature.

3. Coloring 10 ml of a 3% by weight polyacrylate-containing aqueous solution of hydrogen peroxide was optionally used as the oxidative developing solution. The catalyst according to the invention was predissolved in a few drops of water, optionally added to the developing solution and then incorporated in the coloring cream.

The ready-to-use preparation was then applied to a hair tress of the "Kerling Naturweiß" type (1.5 g preparation per g hair), left thereon for 30 minutes and then rinsed out with water.

Coloring was carried out under the conditions indicated in the following Table:

| Metal | Concentration | Ligand | $H_2O_2$ Concentration | pH | Evaluation |
|---|---|---|---|---|---|
| Ruthenium | 200 ppm | DBU | 0.35% by weight | 9.0 | Full color |
| Ruthenium | 200 ppm | DBU | 1.5% by weight | 7.0 | Full color |
| Copper | 200 ppm | DBU | — | 9.0 | Full color |
| Copper | 200 ppm | DBU | 1.5% by weight | 7.0 | Full color |
| — | — | — | 1.5% by weight | 7.0 | No color |
| — | — | — | 1.5% by weight | 9.0 | Full color |

What is claimed is:

1. A composition for coloring keratin fibers comprising
   (a) one or more clathrate compounds having cavities;
   (b) one or more transition metal complexes, located within the cavities of the clathrate compounds, wherein the transition metal complex comprises (i) from 0.0001 weight percent to 1.0 weight percent, based on the total weight of the composition, of at least one transition metal cation having at least two stable oxidation stages, and (ii) at least one multidentate ligand complexed with the transition metal cation; and
   (c) at least one dye precursor for coloring keratin fibers.

2. The composition of claim 1 wherein the clathrate compounds comprise one or more zeolites of type A, K, L, P-L, O, T, X, Y or Ω or mixtures thereof.

3. The composition of claim 2 wherein the transition metal cation is selected from iron, cobalt, copper, manganese, molybdenum, ruthenium or vanadium or combinations thereof.

4. The composition of claim 3 wherein the transition metal cation is copper or ruthenium or combinations thereof.

5. The composition of claim 3 wherein the ligand has at least one nitrogen atom as a coordination site.

6. The composition of claim 5 wherein the ligand is selected from 1,4,8,11-tetraazacyclotetradecane, 1,8-diazabicyclo[5.4.0]undec-7-ene (1,5-5), ethylenediamine, nitrilotriacetic acid, tris(aminoethyl)amine, tris(aminomethyl)methane, 1,3,5-triaminocyclohexane or pyridine-2,6-dicarboxylic acid, or combinations thereof.

7. The composition of claim 3 wherein the ligand has at least one aromatic coordination site.

8. The composition of claim 7 wherein the ligand with at least one aromatic coordination site comprises 2,2':6',2''-terpyridine, 1,10-phenanthroline, tris(2-pyridylmethyl)amine, tris(2-pyridylethyl)amine or N-carboxymethyl-N-(2-pyridylmethyl)glycine, or combinations thereof.

9. The composition of claim 1 wherein the transition metal cation is selected from iron, cobalt, copper, manganese, molybdenum, ruthenium or vanadium, or combinations thereof.

10. The composition of claim 1 wherein the ligand has at least one nitrogen atom as a coordination site, or has at least one aromatic coordination site, or combinations thereof.

11. The composition of claim 1 wherein the dye precursor comprises at least one primary intermediate oxidation dye precursor.

12. The composition of claim 11 wherein the dye precursor comprises at least one secondary intermediate oxidative dye precursor.

13. The composition of claim 1 wherein the dye precursor comprises at least one indole derivative, or indoline derivative, or combinations thereof.

14. The composition of claim 13 wherein the dye precursor comprises at least one secondary intermediate oxidative dye precursor.

15. The composition of claim 1 wherein the composition has a pH value of 6.5 to 8.

16. The composition of claim 1 wherein the composition is free of chemical oxidizing agents.

17. A method for coloring keratin fibers comprising applying a composition to keratin fibers, wherein the composition comprises
   (a) one or more clathrate compounds having cavities; and
   (b) one or more transition metal complexes, located within the cavities of the clathrate compounds, wherein the transition metal complex comprises (i) from 0.0001 weight percent to 1.0 weight percent, based on the total weight of the composition, of at least one transition metal cation having at least two stable oxidation stages, and (ii) at least one multidentate ligand complexed with the transition metal cation.

18. The method of claim 17 wherein the composition further comprises at least one dye precursor.

19. The method of claim 18 wherein the clathrate compounds comprise one or more zeolites of type A, K, L, P-L, O, T, X, Y or Ω or mixtures thereof.

* * * * *

UNITED STATES PATENT AND TRADEMARK OFFICE
CERTIFICATE OF CORRECTION

PATENT NO. : 6,648,925 B1
DATED : November 18, 2003
INVENTOR(S) : Mayer et al.

It is certified that error appears in the above-identified patent and that said Letters Patent is hereby corrected as shown below:

Title page,
Item [86], after "§ 371 (c)(1), (2), (4) Date:", delete "Sep. 26, 2001", and insert therefore -- Sep. 25, 2001 --.

Signed and Sealed this

Twelfth Day of October, 2004

JON W. DUDAS
*Director of the United States Patent and Trademark Office*